(12) United States Patent
Lee

(10) Patent No.: US 10,857,288 B2
(45) Date of Patent: Dec. 8, 2020

(54) DISPOSABLE INFUSION SYSTEM ENCLOSURE

(71) Applicant: Infutronix LLC, Natick, MA (US)

(72) Inventor: Frederick Lee, Weston, MA (US)

(73) Assignee: Infutronix LLC, Natick, MA (US)

( * ) Notice: Subject to any disclaimer, the term of this patent is extended or adjusted under 35 U.S.C. 154(b) by 161 days.

(21) Appl. No.: 16/135,603

(22) Filed: Sep. 19, 2018

(65) Prior Publication Data

US 2019/0083700 A1 Mar. 21, 2019

Related U.S. Application Data

(60) Provisional application No. 62/560,758, filed on Sep. 20, 2017.

(51) Int. Cl.
| | | |
|---|---|---|
| *A61M 5/14* | (2006.01) | |
| *A61J 1/10* | (2006.01) | |
| *A61M 5/168* | (2006.01) | |
| *A61M 5/142* | (2006.01) | |
| *A61M 5/50* | (2006.01) | |
| *A61M 5/00* | (2006.01) | |

(52) U.S. Cl.
CPC .............. *A61M 5/1413* (2013.01); *A61J 1/10* (2013.01); *A61M 5/002* (2013.01); *A61M 5/142* (2013.01); *A61M 5/1417* (2013.01); *A61M 5/14212* (2013.01); *A61M 5/16813* (2013.01); *A61M 5/5086* (2013.01); *A61M 2005/14208* (2013.01); *A61M 2205/273* (2013.01); *A61M 2205/583* (2013.01); *A61M 2209/06* (2013.01)

(58) Field of Classification Search
CPC .............. A61M 5/1414; A61M 5/1415; A61M 5/1417; A61J 1/10; A61J 1/14; A61J 1/1462; A61J 1/1493; A61B 50/00; A61B 50/30; A61B 50/31; A61B 2050/3008
See application file for complete search history.

(56) References Cited

U.S. PATENT DOCUMENTS 5,879,143 A * 3/1999 Cote .................... A61M 5/1413
                                                      417/474

OTHER PUBLICATIONS

AmbIT Infusion Pumps Product Catalog, Website, www.ambitpump.com/products/catalog.

* cited by examiner

*Primary Examiner* — Laura A Bouchelle
(74) *Attorney, Agent, or Firm* — Boyle Fredrickson S.C.

(57) ABSTRACT

A one-time use plastic disposable lockbox enclosing an infusion system including the infusion device, method of delivery such as tubing, and source reservoir such as a fluid bag or syringe is provided. The lockbox includes first and second thermoplastic shells joinable along a separation plane to define a housing. The housing carries an IV bag volume abutting a periphery of a filled standard IV bag to restrain movement of that IV bag along the separation plane and a pump volume abutting a periphery of an IV pump to restrain movement of that IV pump along the separation plane. A channel extends between the pump volume and an exterior of the housing to allow egress of a standard IV line from the housing.

20 Claims, 5 Drawing Sheets

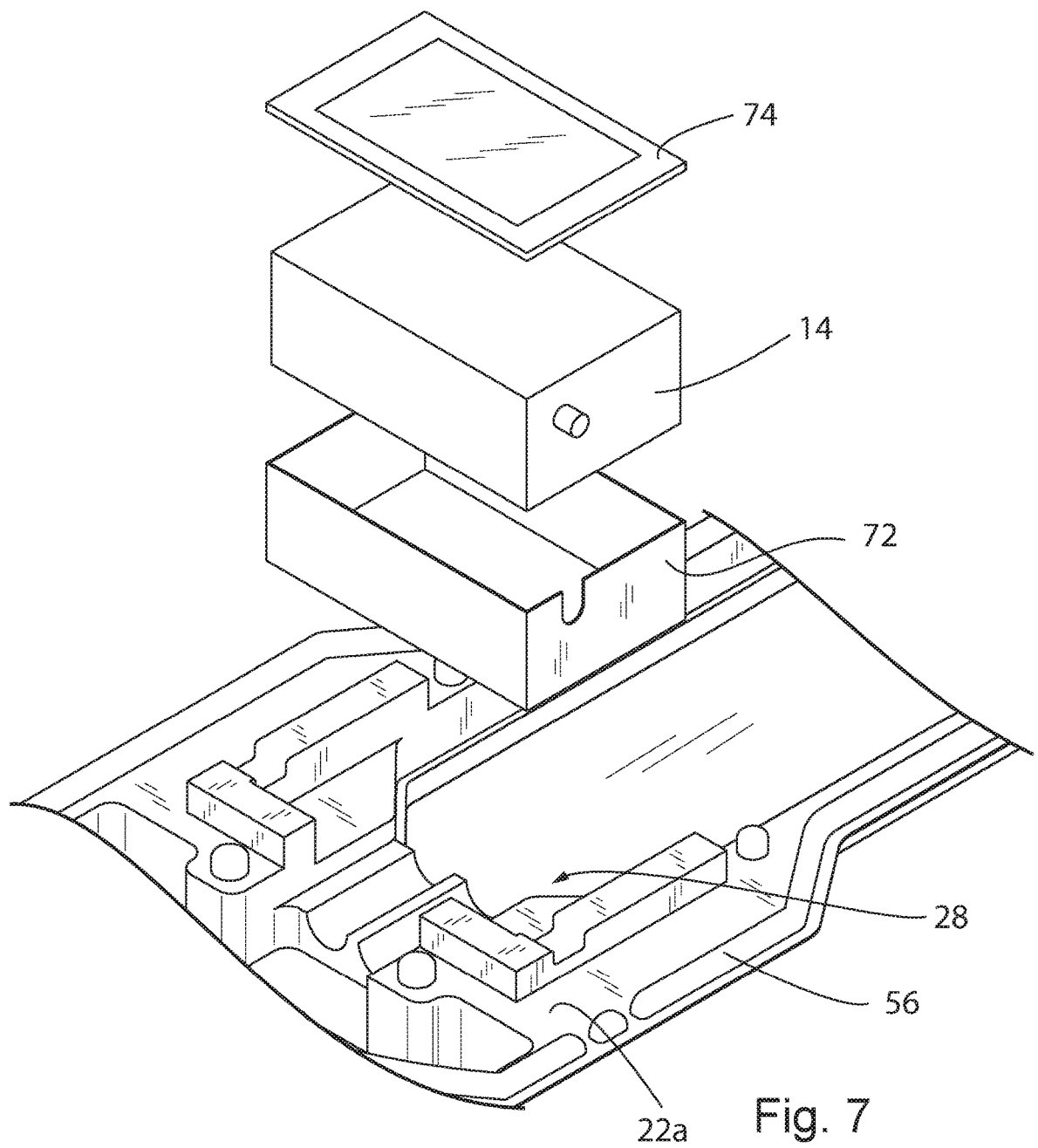

DISPOSABLE INFUSION SYSTEM ENCLOSURE

CROSS REFERENCE TO RELATED APPLICATION

This application claims the benefit of U.S. provisional application No. 62/560758, filed Sep. 20, 2017.

BACKGROUND OF THE INVENTION

The present invention relates to infusion systems and disposable enclosures for infusion devices along with single-use fluid reservoirs including flexible bags or syringes.

Medical devices frequently undergo a decontamination procedure after each use to isolate possible infection from a previous patient and prepare the device for the next patient. This decontamination process can be costly in both labor and time for any facility. There is a need for not only a contamination-adverse design of infusion pumps, but also protective enclosures to prevent contamination.

Infusion systems generally include a fluid reservoir from which the device pulls from to deliver to the patient. These fluid reservoirs are either part of the pump or external bags or syringes attached to the administration set. Infusion systems can also come with multiple pieces that may need assembly at the time of use, however, these pieces can often be unintentionally lost or separated through the transport process.

In several applications, the fluid reservoirs are filled with controlled substances such as narcotics, which can be simply withdrawn with a syringe if left unprotected. These controlled substances need to be difficult to access. Medical professionals must see any trace of unauthorized withdrawal or misuse of the controlled substance in the fluid reservoir.

Other fluid medications, such as the ones used in chemotherapy, are harmful when in direct contact with the skin or orifices. If a leakage occurs in any portion of the fluid delivery process, there must be a method of containing the expelled fluid and mitigating unintended impact.

If the infusion system is being used in an ambulatory or transport environment, the fluid bag, conduit, and pump can be subject to damage from foreign objects. A general enclosure for all parts would provide additional protection from punctures, tears, and breaks. The present invention aims to solve the some or all of the above problems all while staying affordable and comfortable.

SUMMARY OF THE INVENTION

The present invention is a one-time use plastic disposable lockbox enclosing an infusion system including the infusion device, method of delivery such as tubing, and source reservoir such as a fluid bag or syringe.

This single-use lockbox removes the need for labor and resource intensive decontamination procedures due to its disposable nature. When the fluid reservoir, tubing, and pump are removed from the enclosure it will then become non-functional and will be discarded along with other single-use components into a proper bio-hazard removal bin.

In one embodiment, the present invention may be an infusion pump enclosure system including first and second thermoplastic shells joinable along a separation plane to define a housing and providing within the housing an IV bag volume defined by retaining surfaces of at least one shell extending perpendicular to the separation plane to abut a periphery of a filled standard IV bag to restrain movement of that IV bag along the separation plane; a pump volume defined by retaining surfaces of at least one shell extending perpendicular to the separation plane to abut a periphery of an IV pump to restrain movement of that IV pump along the separation plane; and a channel extending between the pump volume and an exterior of the housing and sized to allow egress of a standard IV line from the housing.

It is thus a feature of at least one embodiment of the invention to enable pharmacy and clinicians to bundle necessary accessories, medication, and devices within this pre-packaged lockbox solution to be operated at point of care and increase overall workflow efficiency.

The housing may provide a hanger hole extending perpendicular to the separation plane to receive a hanger and positioned above the IV bag volume, wherein the IV bag volume is further positioned above the pump volume.

It is thus a feature of at least one embodiment of the invention to suspend the lockbox from an IV pole for hospital use. Variations of the design may also make the lockbox comfortable to wear for ambulatory use.

The IV bag volume may provide at an end closest to the hanger hole, an inwardly extending peg adapted to support a suspension opening of an IV bag support. A shell opposite a shell providing the inwardly extending peg may provide at least one retention post holding the IV bag suspension opening in engagement with the inwardly extending peg when the shells are joined.

It is thus a feature of at least one embodiment of the invention to suspend the IV bag above the pump for gravitational pump assist and in a secured position within the enclosure.

The first and second shells at an end of the housing removed from the hanger hole may interfit to provide a seal resistant to liquid leakage and further including a leakage retention volume adjacent to the seal.

It is thus a feature of at least one embodiment of the invention to include a compartment in which the connection between the fluid reservoir and tubing will be placed and leakages will be contained to that compartment preventing potentially hazardous contact to patients and devices.

The first and second shells may further provide a second channel communicating between the IV bag volume and the pump volume for supporting an IV line connected between the IV bag and the IV pump. A third channel may extend between the exterior of the housing and the bag volume to allow ingress of a standard IV line into the housing. At least one of the channel and third channel may be sized to compress the IV line without blocking fluid flow through the IV line thereby restraining the IV line against movement along the separation plane.

It is thus a feature of at least one embodiment of the invention to allow for conventional delivery of drugs through the IV line while keeping the IV bag, IV pump and IV lines contained within or connected to the lockbox to prevent tampering.

At least one of the first and second shells forming the IV bag volume may provide a first port groove extending outwardly from the IV bag volume to receive a first port of the IV bag and a second port groove extending outwardly from the IV bag volume to receive a second port of the IV bag when the IV bag is retained within the IV bag volume.

It is thus a feature of at least one embodiment of the invention to support a standard IV bag's connection ports for conventional IV drug preparation injecting a drug into the bag containing intravenous fluids such as saline and delivery of those drugs through a pump.

The retaining surfaces of the IV bag volume may form an outwardly extending depression in the first shell and the retaining surfaces of the pump volume form an outwardly extending depression in the second shell. The housing may form a clamshell container having the first shell and the second shell joined at a living hinge.

It is thus a feature of at least one embodiment of the invention to allow the pharmacist to easily and quickly bundle the accessories into the lockbox, having a width accommodating the dimensions of the IV bag and IV pump, and without having to locate matching shells.

An outer periphery of the housing may provide in molded bosses of at least one shell received by in molded sockets of the opposite shell in an engaged state. An outer periphery of the housing may provide an upstanding rib of at least one shell interengaging with the opposite shell to form a liquid resistant seal in an engaged state.

It is thus a feature of at least one embodiment of the invention to provide multiple compartments allowing accessories to be placed inside the lockbox that can be opened separately when needed.

An outer periphery of the housing provides first outwardly extending tabs extending from at least one shell attachable to second outwardly extending tabs extending from the opposite shell wherein the first and second tabs are adapted to provide visual indication of separation of the first and second tabs. A distal end of the first and second outwardly extending tabs may be removable permitting the first and second outwardly extending tabs to be separable.

It is thus a feature of at least one embodiment of the invention to prevent open access to the fluid reservoir, and if tampered with, will show an unrepairable trace of tamper.

At least one shell forming a front or rear wall abutting the pump volume has depressions aligning with control buttons of the pump held within the pump volume.

It is thus a feature of at least one embodiment of the invention to allow for pump operation while the pump in held within the lockbox.

The IV bag volume may have a width between 50 and 150 millimeters and a height between 135 millimeters and 225 millimeters. The pump volume may have a width between 100 and 110 millimeters and a height between 40 and 60 millimeters.

The system may include a filled standard IV bag held in the IV bag volume holding a medicament and providing a first attachment port for fluid communication with the interconnecting IV line.

The system may include a pump unit attachable to the IV bag and held in the pump volume including a housing; an electromechanical pump held by the housing and communicating with the interconnecting IV line to pump fluid to the patient connecting IV line; a pump unit electronic processor held by the housing and communicating with the electromechanical pump and holding a stored program holding a drug delivery rate and drug dose; and control buttons held by an exterior of the housing and for receiving control information.

The enclosure may also be manufactured from gamma-resistant material allowing the contents inside to be fully protected from gamma radiation related therapies.

These particular objects and advantages may apply to only some embodiments falling within the claims and thus do not define the scope of the invention.

BRIEF DESCRIPTION OF THE DRAWINGS

FIG. 7 is an exploded diagram showing the insertion of a gamma resistant container within the enclosure of the present invention surrounding the pump.

DETAILED DESCRIPTION OF THE PREFERRED EMBODIMENT

Figure 1:
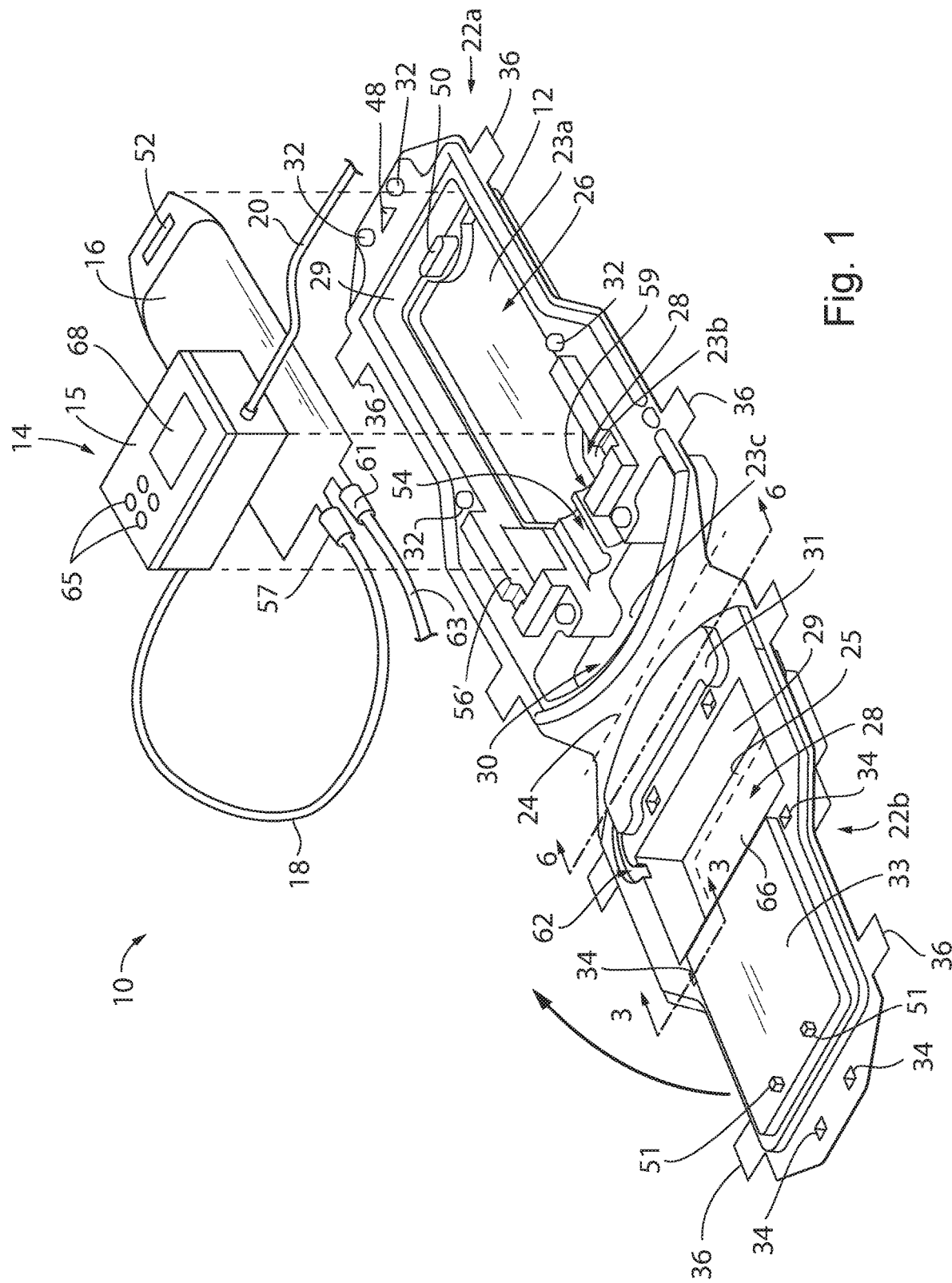
FIG. 1 is an exploded perspective view of an enclosure of the present invention providing two halves in an open state for receiving a medicament bag and pump and to be folded to a closed state around the medicament bag and pump.

Referring now to FIG. 1, an infusion pump enclosure system 10 may include a disposable housing 12 for receiving an infusion pump 14, a medicament bag 16, interconnecting IV line 18, and portion of a patient connecting IV line 20.

The disposable housing 12 in one embodiment may be in the form of a pre-sterilized "clamshell" container having a first and second half 22a and 22b joined at a hinge line 24 in a "living hinge" so they can be folded together at the hinge line 24 together to provide an enclosure. The first and second half 22a and 22b join to close in a closed state along a separation plane 27. In one embodiment, the disposable housing 12 may be constructed of a sheet of transparent thermoplastic such as polystyrene, polyester, PET or PVC, for example, having a thickness from 0.007 inches to 0.047 inches and formed by low-cost tooling using thermoforming or vacuum forming.

Figure 2:
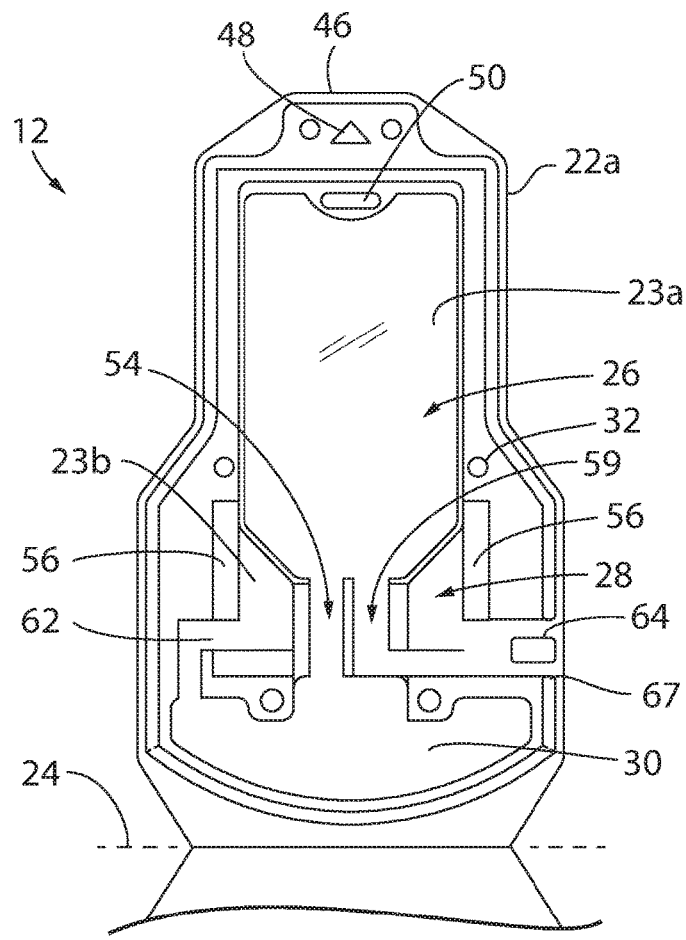
FIG. 2 is a top plan view of one half of the enclosure of FIG. 1 showing the various compartments formed therein.

Referring also to FIG. 2, each of the first and second halves 22a and 22b may have in-molded elements to provide each of: a bag holding volume 26, a pump holding volume 28 and a leak reservoir 30. The in-molded elements may be defined by retaining walls 29 extending perpendicular to the separation plane 27 between the first and second halves 22a and 22b and abutting an outer periphery of the held infusion pump 14 and medicament bag 16, respectively, to restrain movement therein. For this purpose, first half 22a may have depressions 23a, 23b and 23c providing portions of the bag holding volume 26, the pump holding volume 28 and the leak reservoir 30 respectively. Similarly, the second half 22b may have a depression 25 for the pump holding volume 28, a raised plug section 31 for the leak reservoir 30 and a flat plate section 33 for the bag holding volume 26 providing the completing walls for these volumes. The depressions 23a, 23b, 23c may extend outwardly, away from the separation plane 27 and the raised tabs may extend inwardly toward the separation plane 27, when in the closed state. It should be understood that these in-molded components of each of the first half 22a and second half 22b are joined when the halves 22a and 22b are brought together with the hinging of the disposable enclosure element about hinge line 24 to define enclosed respective bag holding volume 26, pump holding volume 28, and leak reservoir 30.

An outer periphery of the first half 22a may support interengaging in-molded bosses 32 received by corresponding in-molded sockets 34 in the second half 22b that serve to retain the halves 22a and 22b together. Likewise, tabs 36 may extend outwardly from each periphery of the first half 22a and second half 22b to abut when the halves are brought together about the hinge line 24 so that the tabs can be affixed to each other to hold the halves 22a and 22b together.

Figure 3:
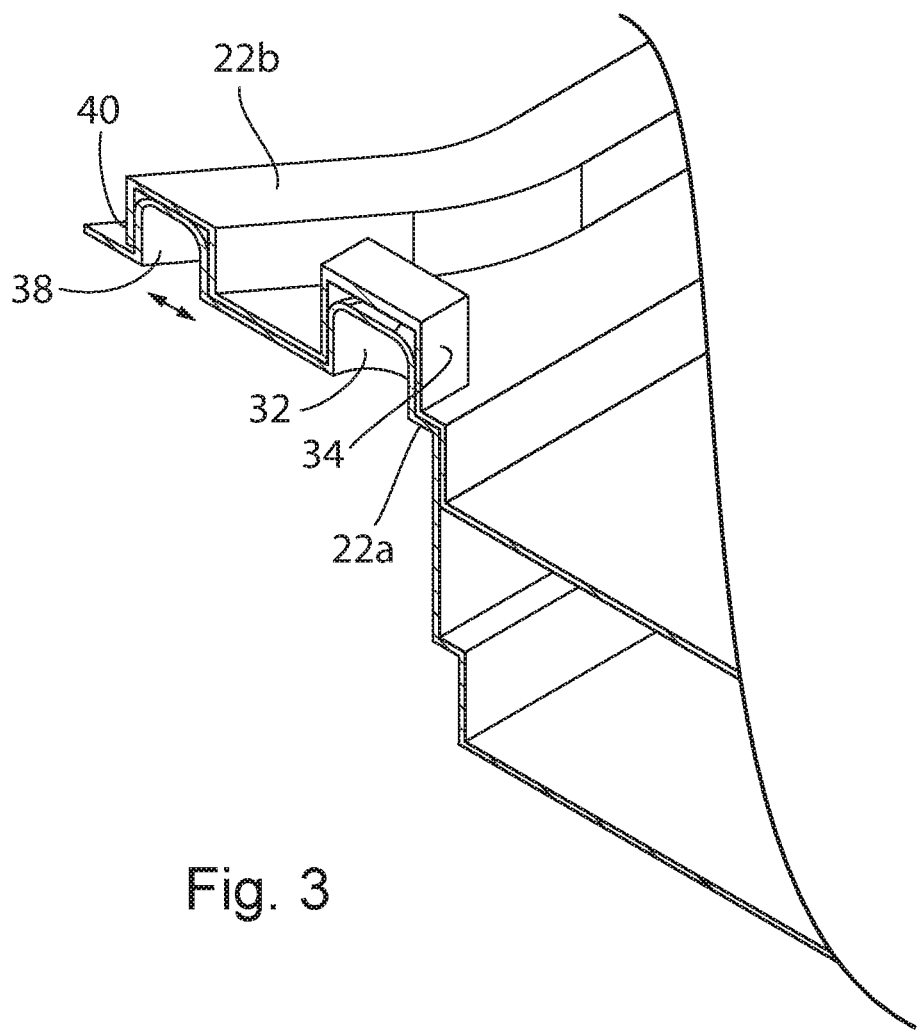
FIG. 3 is a cross-sectional view along line 3-3 of FIG. 1 when the enclosure is in the closed form showing the interlocking of the edges of the enclosure and a tamper resistant attachment when the two halves are assembled together.

Referring now to FIG. 3, a periphery of first half 22a may provide for an upstanding rib 38 formed by a U-shaped bend in the material of the half 22a. This upstanding rib 38 may be received by corresponding channel 40 formed in the periphery of the half 22b that serves to compress the rib 38 when the two are interengaged to provide a liquid resistant seal in the closed state. In this closed state, the bosses 32 are tightly received in the sockets 34 and may be ultrasonically welded together to provide for tamper resistance after the halves are interengaged. The upstanding rib 38 may also simply abut the periphery of the half 22b to contact the rib 38 in a manner that provides a liquid resistant seal in the closed state.

Figure 4:
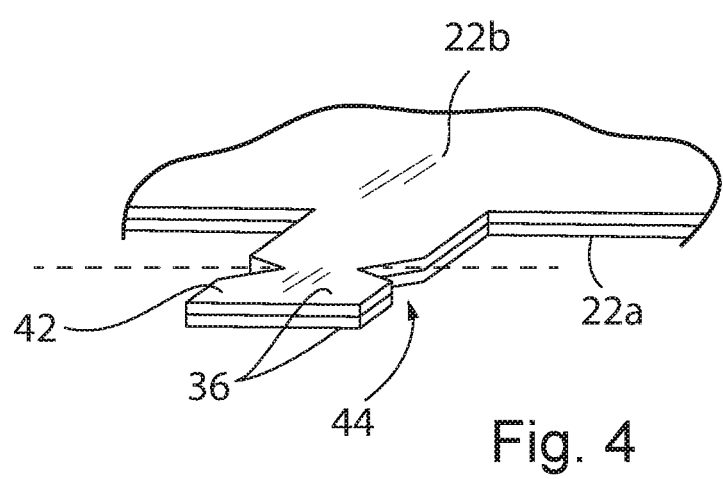
FIG. 4 is a fragmentary view of a tab for attaching the two halves together in a way that is tamper evident.

Referring to FIG. 4, likewise tabs 36 on halves 22a and 22b may be welded or glued together at attachment points 42 to retain the halves 22a and 22b. In this regard, separation of the halves may be effected by tearing or removing an outer portion of the attached tabs beyond a tear starter notch 44 thereby removing the attachment point 42 allowing the halves 22a and 22b to separate but providing a visible indication that the halves have been separated evidenced by missing portions of the tabs 36. In this regard, the tabs 36 may be used instead of the bosses 32 and sockets 34 and in this way removal of the tabs 36 may be more evident because the clamshell halves are no longer retained together. It will also be understood that the attachment points 42 on the tabs 36 may be in the form of a socket 34 and bosses 32 if desired.

Referring again to FIGS. 1 and 2, an upper end of the disposable housing 12 formed of the abutting of the opposite ends of the halves 22a and 22b furthest from the hinge line 24 may provide a hang tab 46 having an opening 48 so that the disposable housing 12 may be supported on a standard IV pole. Within the bag holding volume 26, an in-molded feature may provide an upwardly extending peg 50 formed in the half 22a that may in turn support the bag 16 at a bag support opening 52 (shown in FIG. 1) within the disposable housing 12. The upwardly extending peg 50 may be received by upwardly extending flanking retention posts 51 formed in the half 22b that abut the outer ends of the upwardly extending peg 50 when the two are interengaged to provide a secured bag support in the closed state.

A lower end of the bag holding volume 26, as normally oriented during use, provides a downwardly extending groove 54 that may receive the "spike" 57 of the IV bag 16 providing attachment point to IV lines. This groove 54 passes beneath the lower wall providing the pump holding volume 28 in half 22a so that the end of the spike 57 that will attach to the interconnecting IV line 18 may be in the leak reservoir 30 positioned below the pump holding volume 28 to prevent back leakage onto the pump 14. A lower end of the bag holding volume 26, as normally oriented during use, may also provide a second downwardly extending groove 59 that may receive a medication port 61 of the IV bag 16 providing ingress of drugs into the IV bag 16. This second groove 59 passes beneath the lower wall providing the pump holding volume 28 in half 22a so that the end of the medication port 61 that will attach to a medication ingress IV line 63 providing a flow of drugs from an external drug container into the bag 16 may be in the leak reservoir 30 positioned below the pump holding volume 28 to prevent back leakage onto the pump 14.

The IV bag 16 may be a standard medical IV bag having, for example, the following dimensions and fluid capacity known in the art: 25 ml (50×135 mm), 50 ml (50×135 mm), 100 ml (100×135 mm), 250 ml (135×160 mm), 500 ml (148×220 mm). In this respect, the bag holding volume 26 may have dimensions that are slightly larger than the dimensions of the IV bag 16 in order to contain the bag 16 but provide abutting retaining walls 29 to prevent movement of the IV bag 16. For example, the bag holding volume 26 may have a width that is between 50 and 150 mm, or about 1-5 mm larger than a width of the bag 16, and a height that is between 135 and 225 mm, or about 1-5 mm larger than a height of the bag 16, and depending on the size of the IV bag 16 containing IV fluids such as saline.

Figure 5:
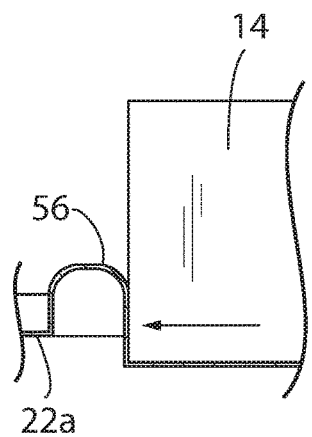
FIG. 5 is a cross-sectional view along line 5-5 of FIG. 2 showing an integrated shock absorbing bumper for surrounding the pump.

Referring also to FIG. 5, pump holding volume 28 may be surrounded by an in-molded feature providing a bumper 56 abutting the outer edges of the pump 14 to provide shock resistance to the pump by flexure of the inner and outer walls of the U-shaped bumper 56 toward and away from each other. The pump 14 may be defined by a rectangular enclosure 15 being approximately 108 mm by 58 mm by 40 mm. In this respect, the pump holding volume 28 may have dimensions that are slightly larger, for example, 1-5 mm larger, than the dimensions of the enclosure in order to contain the pump 14 but still providing abutting walls to prevent movement of the pump 14. For example, the pump holding volume 28 may have a width that is between 100 and 110 mm and a height that is between 40 mm and 60 mm. The pump 14 may include an electromechanical pump communicating with the interconnecting IV line 18 to pump fluid to the patient connecting IV line 20, an electronic processor and communicating with the electromechanical pump and holding a stored program holding a drug delivery rate and drug dose; and control buttons held by an exterior of the pump enclosure 15 for receiving control information.

In order to provide compact construction of the disposable housing 12, a lower end of the bag holding volume 26 may overlap with the pump holding volume 28 to allow the IV bag 16 and pump 14 to be stacked perpendicular to the separation plane 27 within the disposable housing 12 and therefore saving space along a length of the disposable housing 12 along the separation plane 27. In this respect, the disposable housing 12 has a width defined by a distance between oppositely opposed in molded components of the first and second halves 22a and 22b supporting a dimension of the stacked IV bag 16 and pump 14 therein.

Figure 6:
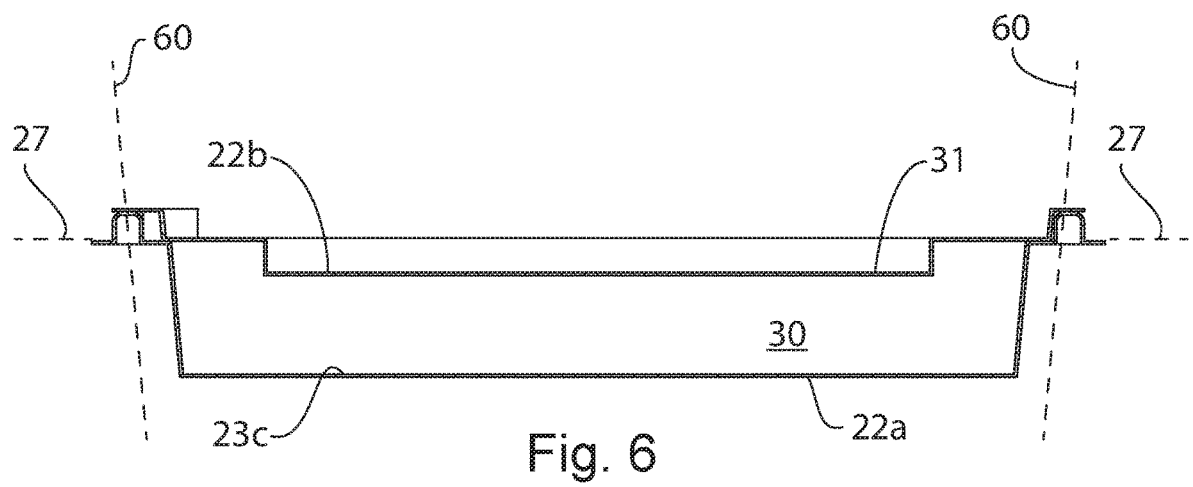
FIG. 6 is a cross-sectional view along line 6-6 of FIG. 1 showing interlocking of compartment halves in a leak resistant volume.

Referring to FIGS. 1, 2, and 6, the leak reservoir 30 may be formed by the inter-engagement of a pocket formed in half 22a and raised plug section 31 formed in half 22b whose interengaging walls may be canted as indicated by lines 60 to provide a wedging engagement reducing leakage.

Referring again to FIG. 2, a channel 62 may be formed in one or both of the halves 22a and 22b between the leak reservoir 30 and the pump holding volume 28 to allow the IV line 18 to be interconnected to the spike 57 within the leak reservoir 30 (and thus for leakage at this interconnection to be contained therein) while allowing the IV line 18 to communicate with the pump 14 in the pump holding volume 28. Similarly, the pump holding volume 28 may provide an open channel 64 leading out of the disposable housing 12 allowing egress of the patient connecting IV line 20. The open channel 64 may be sized to restrain lateral movement of the patient connecting IV line 20 without blocking fluid flow through the patient connecting IV line 20. Generally, this open channel 64 will be substantially above the interconnection between the spike 57 and IV line 18 so as to prevent liquid captured by the leak reservoir 30 from escaping from the disposable housing 12 through this open channel 64. Similarly, the bag holding volume 26 may provide a second open channel 67 leading into the disposable housing 12 allowing ingress of the medication ingress IV line 63. The second open channel 67 may be sized to compress the medication ingress IV line 63 without blocking fluid flow through the medication ingress connection IV line thereby restraining the IV line against movement along the separation plane 27. The second open channel 67 may be positioned adjacent to and generally parallel to the open channel 64.

Figure 8:
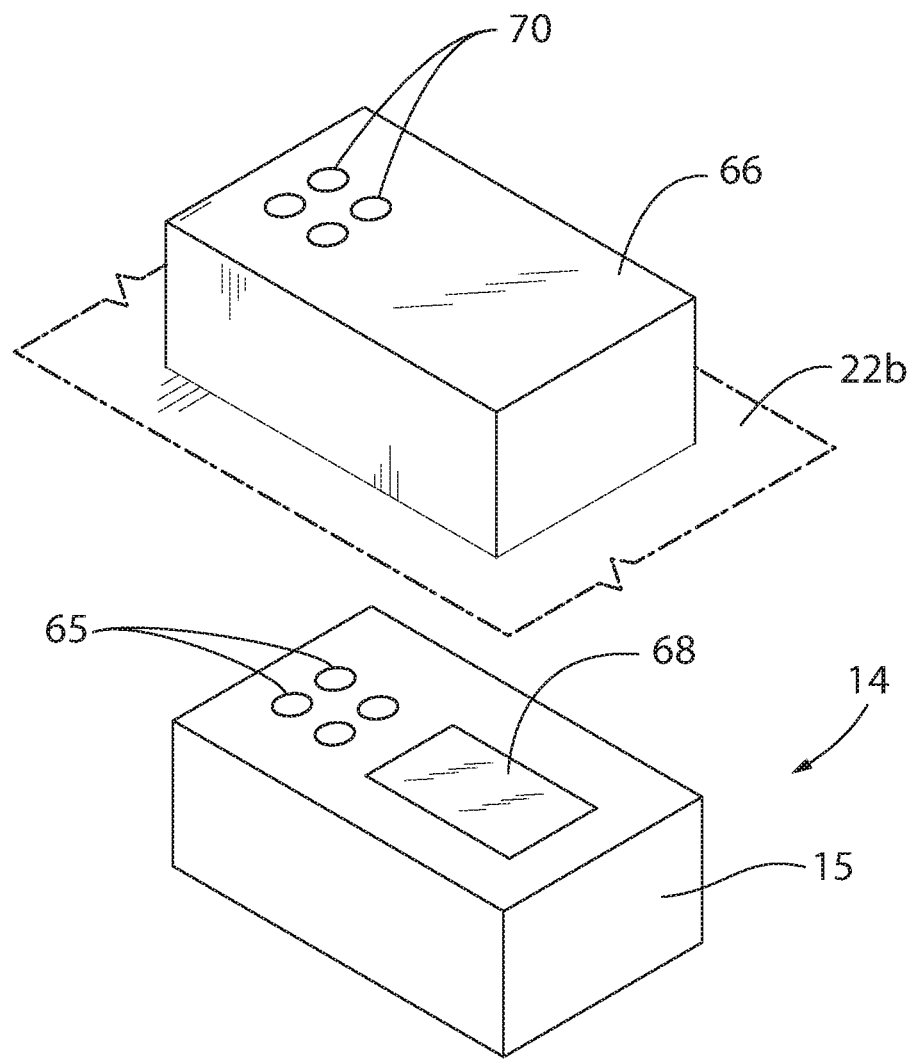
FIG. 8 is a fragmentary detail of a portion of the container overlying a control panel of the pump showing embossing in transparent areas for operation of the pump through the enclosure.

Referring again to FIG. 1, a lower wall 66 of the depression 25 may be perforated for removal or may be cut to provide an aperture to allow access to the control buttons 65 of the pump 14 and viewing of the control display 68 of the pump 14, for example, and LCD screen of the pump 14. Conversely as shown in FIG. 8, this lower wall 66 to be constructed of a flexible and transparent material to allow viewing of the control display 68 therethrough and activation of the control buttons 65 by deformation of that wall 66. For this purpose, depressions 70 may be in-molded into the wall 66 aligned with the control buttons 65 so as to allow slight flexing of the upper wall 66 to activate specific control buttons 65 readily through the downwardly extending protrusions caused by the depressions 70.

Referring now to FIG. 7, the pump holding volume 28 may be sized to receive a gamma radiation resistant container 72 into which the pump 14 may be installed and, for example, covered by a lid 74. This assembly of container 72, lid 74, and pump 14 may then be encased and surrounded within first and second halves 22a and 22b of the enclosure. This gamma resistant container 72 and lid 74, for example, may be constructed of a material blocking damage to the pump 14 caused by gamma radiation, for example, as constructed of a high molecular weight material such as lead. By enclosing the container 72 and lid 74 within the material of the disposable housing 12, sterilization of this material of the container 72 and lid 74 and protection of the individual from possible toxic components of this material are provided.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

I claim:

1. An infusion pump enclosure system comprising:
    first and second thermoplastic shells joinable along a separation plane to define a housing and providing within the housing:
    an IV bag volume defined by retaining surfaces of at least one shell extending perpendicular to the separation plane to abut a periphery of a filled standard IV bag to restrain movement of that IV bag along the separation plane;
    a pump volume defined by retaining surfaces of at least one shell extending perpendicular to the separation plane to abut a periphery of an IV pump to restrain movement of that IV pump along the separation plane; and
    a channel extending between the pump volume and an exterior of the housing and sized to allow egress of a standard IV line from the housing
    wherein the housing provides a hanger hole extending perpendicular to the separation plane to receive a hanger and positioned above the IV bag volume, wherein the IV bag volume is further positioned above the pump volume;
    wherein the first and second shells at an end of the housing removed from the hanger hole interfit to provide a seal resistant to liquid leakage and further including a leakage retention volume adjacent to the seal.

2. The pump of claim 1 wherein the IV bag volume provides at an end closest to the hanger hole, an inwardly extending peg adapted to support a suspension opening of an IV bag support.

3. The pump of claim 2 wherein a shell opposite a shell providing the inwardly extending peg provides at least one retention post holding the IV bag suspension opening in engagement with the inwardly extending peg when the shells are joined.

4. The pump of claim 1 wherein the first and second shells further provide a second channel communicating between the IV bag volume and the pump volume for supporting an IV line connected between the IV bag and the IV pump.

5. The pump of claim 4 further comprising a third channel extending between the exterior of the housing and the bag volume to allow ingress of a standard IV line into the housing.

6. The pump of claim 5 wherein at least one of the channel and third channel is sized to compress the IV line without blocking fluid flow through the IV line thereby restraining the IV line against movement along the separation plane.

7. The pump of claim 1 wherein at least one of the first and second shells forming the IV bag volume provides a first groove extending outwardly from the IV bag volume to receive a first port of the IV bag and a second groove extending outwardly from the IV bag volume to receive a second port of the IV bag when the IV bag is retained within the IV bag volume.

8. The pump of claim 1 wherein the retaining surfaces of the IV bag volume form an outwardly extending depression in the first shell and the retaining surfaces of the pump volume form an outwardly extending depression in the second shell.

9. The pump of claim 1 wherein an outer periphery of the housing provides in molded bosses of at least one shell received by in molded sockets of an opposite shell in an engaged state.

10. The pump of claim 1 wherein an outer periphery of the housing provides an upstanding rib of at least one shell interengaging with an opposite shell to form a liquid resistant seal in an engaged state.

11. The pump of claim 1 wherein an outer periphery of the housing provides first outwardly extending tabs extending from at least one shell attachable to second outwardly extending tabs extending from an opposite shell wherein the first and second tabs are adapted to provide visual indication of separation of the first and second tabs.

12. The pump of claim 11 wherein a distal end of the first and second outwardly extending tabs are removable permitting the first and second outwardly extending tabs to be separable.

13. The pump of claim 1 wherein the IV bag volume has a width between 50 and 150 millimeters and a height between 135 millimeters and 225 millimeters.

14. The pump of claim 1 wherein the pump volume has a width between 100 and 110 millimeters and a height between 40 and 60 millimeters.

15. The pump of claim 1 further comprising a filled standard IV bag held in the IV bag volume holding a medicament and providing a first attachment port for fluid communication with an interconnecting IV line.

16. The pump of claim 1 further comprising a pump unit attachable to the IV bag and held in the pump volume including
a housing;
an electromechanical pump held by the housing and communicating with an interconnecting IV line to pump fluid to a patient connecting IV line;
a pump unit electronic processor held by the housing and communicating with the electromechanical pump and holding a stored program holding a drug delivery rate and drug dose; and
control buttons held by an exterior of the housing and for receiving control information.

17. An infusion pump enclosure system comprising:
first and second thermoplastic shells joinable along a separation plane to define a housing and providing within the housing:
an IV bag volume defined by retaining surfaces of at least one shell extending perpendicular to the separation plane to abut a periphery of a filled standard IV bag to restrain movement of that IV bag along the separation plane;
a pump volume defined by retaining surfaces of at least one shell extending perpendicular to the separation plane to abut a periphery of an IV pump to restrain movement of that IV pump along the separation plane; and
a channel extending between the pump volume and an exterior of the housing and sized to allow egress of a standard IV line from the housing;
wherein the housing forms a clam shell container having the first shell and the second shell joined at a living hinge.

18. The pump of claim 17 wherein an outer periphery of the housing provides an upstanding rib of at least one shell interengaging with an opposite shell to form a liquid resistant seal in an engaged state.

19. An infusion pump enclosure system comprising:
first and second thermoplastic shells joinable along a separation plane to define a housing and providing within the housing:
an IV bag volume defined by retaining surfaces of at least one shell extending perpendicular to the separation plane to abut a periphery of a filled standard IV bag to restrain movement of that IV bag along the separation plane;
a pump volume defined by retaining surfaces of at least one shell extending perpendicular to the separation plane to abut a periphery of an IV pump to restrain movement of that IV pump along the separation plane; and
a channel extending between the pump volume and an exterior of the housing and sized to allow egress of a standard IV line from the housing;
wherein at least one shell forming a front or rear wall abutting the pump volume has depressions aligning with control buttons of the pump held within the pump volume.

20. The pump of claim 19 wherein the first and second thermoplastic shells are formed by a thermoforming process.

* * * * *